(12) United States Patent
O'Connor

(10) Patent No.: US 10,792,085 B2
(45) Date of Patent: Oct. 6, 2020

(54) METHOD AND APPARATUS FOR PERFORMING CRYOTHERAPY OF DISTAL LUNG LESIONS

(71) Applicant: CSA Medical, Inc., Lexington, MA (US)

(72) Inventor: John P. O'Connor, Andover, MA (US)

(73) Assignee: CSA Medical, Inc., Lexington, MA (US)

(*) Notice: Subject to any disclaimer, the term of this patent is extended or adjusted under 35 U.S.C. 154(b) by 257 days.

(21) Appl. No.: 15/791,042

(22) Filed: Oct. 23, 2017

(65) Prior Publication Data

US 2018/0110555 A1  Apr. 26, 2018

Related U.S. Application Data

(60) Provisional application No. 62/411,889, filed on Oct. 24, 2016.

(51) Int. Cl.

| | | |
|---|---|---|
| *A61B 18/02* | (2006.01) | |
| *A61B 1/267* | (2006.01) | |
| *A61B 18/00* | (2006.01) | |
| *A61B 34/10* | (2016.01) | |

(Continued)

(52) U.S. Cl.
CPC ........ *A61B 18/0218* (2013.01); *A61B 1/2676* (2013.01); *A61B 18/02* (2013.01); *A61B 34/20* (2016.02); *A61B 2018/00101* (2013.01); *A61B 2018/00541* (2013.01); *A61B 2018/00577* (2013.01); *A61B 2018/00982* (2013.01); *A61B 2018/0212* (2013.01); *A61B 2034/105* (2016.02); *A61B 2034/2051* (2016.02); *A61B 2090/367* (2016.02)

(58) Field of Classification Search
CPC ... A61B 18/0218; A61B 1/2676; A61B 34/20; A61B 2034/2051
See application file for complete search history.

(56) References Cited

U.S. PATENT DOCUMENTS

| | | | |
|---|---|---|---|
| 2009/0011032 A1* | 1/2009 | LePivert | ............... A61B 18/02 424/490 |
| 2009/0163902 A1 | 6/2009 | DeLonzor et al. | |
| 2009/0171203 A1 | 7/2009 | Avital et al. | |

(Continued)

FOREIGN PATENT DOCUMENTS

| | | |
|---|---|---|
| GB | 2507612 A | 5/2014 |
| JP | 2005-224528 A | 4/2010 |

(Continued)

OTHER PUBLICATIONS

International Search Report and Written Opinion dated (Jan. 19, 2018), for PCT/US17/57908 (15 pages).

(Continued)

*Primary Examiner* — Linda C Dvorak
*Assistant Examiner* — Annabeth E Rodriguez

(57) ABSTRACT

The present disclosure relates generally to cryosurgery apparatuses and systems for and methods of treatment of distal lung tissue or lesions, and more particularly to guided cryogenic delivery to a distal treatment area within lung tissue via a low-profile, high pressure, closed-tipped catheter or probe configured to pass through a working channel of a bronchoscope and extend to a distal region of the lung.

18 Claims, 2 Drawing Sheets

(51) Int. Cl.
*A61B 90/00* (2016.01)
*A61B 34/20* (2016.01)

(56) References Cited

U.S. PATENT DOCUMENTS

| | | |
|---|---|---|
| 2010/0016847 A1* | 1/2010 | Fischer ................. A61B 18/02 606/21 |
| 2010/0041949 A1* | 2/2010 | Tolkowsky .......... A61B 1/0052 600/109 |
| 2010/0076421 A1 | 3/2010 | Baust et al. |
| 2010/0249765 A1* | 9/2010 | Johnston ............ A61B 18/0218 606/21 |
| 2013/0231651 A1 | 9/2013 | Burr et al. |
| 2014/0343408 A1 | 11/2014 | Tolkowsky |
| 2015/0066005 A1* | 3/2015 | Fan .................... A61B 18/0218 606/21 |
| 2015/0141985 A1 | 5/2015 | Mayse et al. |
| 2015/0305650 A1 | 10/2015 | Hunter |
| 2016/0051221 A1 | 2/2016 | Dickhans et al. |

FOREIGN PATENT DOCUMENTS

| | | |
|---|---|---|
| JP | 2010-512873 A | 4/2010 |
| JP | 2016-511049 A | 4/2016 |
| WO | 9304647 A | 3/1993 |

OTHER PUBLICATIONS

Office Action dated Jan. 7, 2020 for Japanese application No. 2019-509541, 11 pages.

* cited by examiner

METHOD AND APPARATUS FOR PERFORMING CRYOTHERAPY OF DISTAL LUNG LESIONS

PRIORITY

This application claims the benefit of priority under 35 U.S.C. § 119 to U.S. Provisional Application Ser. No. 62/411,889, filed Oct. 24, 2016, which is incorporated by reference herein in its entirety and for all purposes.

TECHNICAL FIELD

The present disclosure relates generally to cryosurgery apparatuses and systems for and methods of treatment of distal lung tissue or lesions, and more particularly to guided cryogenic delivery to a distal treatment area within lung tissue via a low-profile, high pressure, closed-tipped catheter or probe configured to pass through a working channel of a bronchoscope and extend to a distal region of the lung.

BACKGROUND

The present disclosure relates to methods and devices for cryogenic treatment or ablation of lung tissue or lesions, particularly distal lung tissue or lesions. Cryogenic ablation is conducted by freezing diseased, damaged or otherwise unwanted target tissue. Appropriate target tissue in the lung may include, for example, cancerous or precancerous lesions, tumors (malignant or benign), damaged epithelium, fibroses and any other healthy or diseased distal lung tissue for which cryogenic ablation is desired.

The lung can be partitioned into the airways and parenchyma. The airways form the conduits between the outside world and the primary gas exchanging unit, the alveolus. There are three major groups of intrapulmonary airways; cartilaginous bronchi, membranous bronchioles and gas exchange ducts. Distal airways, are typically defined as airways less than 2 mm in diameter, which are comprised of both membranous bronchioles and gas exchange ducts. The trachea divides into two primary bronchi that enter the lung at each hilum. After entering the lungs, the primary bronchi branch downward and outward repeatedly, giving rise to smaller bronchi, which results in a dramatic increase in the number of airways and a progressive decrease in the diameter of each airway. Eventually, bronchi enter a pulmonary lobule and are then termed a bronchiole. Bronchioles are intralobular airways typically with diameters less than 5 mm that branch into five to seven terminal bronchioles. Each terminal bronchiole subdivides into two or more respiratory bronchioles that transition into alveolar ducts. Alveolar ducts open into atria that communicate with alveolar sacs, which terminate into alveoli. Saclike structures typically measuring about 200 μm in diameter, alveoli can evaginate from respiratory bronchioles, alveolar ducts and alveolar sacs. Distal airways are airways typically of less than 2 mm in diameter that consist of small membranous, terminal and respiratory bronchioles as well as alveolar ducts. The small membranous and terminal bronchioles carry out conductive functions, whereas respiratory bronchioles and alveolar ducts can carry out both conducting and gas exchange functions. Because of the small diameter of distal airways, it has been extremely difficult to access the distal tissues of the lung for diagnosis or treatment. Traditional bronchoscopy has been used to aid in the diagnosis and/or treatment of lung cancer and other lung diseases and disorders; however, this procedure only allows doctors to reach the central regions of the lung. Recent developments in lung navigation technology have allowed physicians to visualize the outermost areas of the lung, but access to treatment of these lung regions is limited by the size of the devices used in treatment.

During operation of a cryosurgery system in the lung, a clinician or other operator delivers a cryogen to the target tissue at the treatment site via a catheter, needle or probe. The application of cryogen causes the target tissue to freeze or "cyrofrost." The temperature range of the cryogen delivered to the target tissue can be from 0° C. to negative (−) 125° C. for so-called pseudo-cryogens and from negative (−) 125° C. to negative (−) 195° C. for true cryogens. This lower temperature can be achieved for example with liquid nitrogen at low pressure.

Cryogenic ablation may be performed by using a system that sprays low-pressure cryogen directly onto target tissue or sprays cryogen within a balloon that is in contact with target tissue. Alternatively, some cryotherapy needles or probes utilize the Joule-Thompson effect, typically using argon gas, to generate a cold region near the tip of the needle or probe. With such needles or probes, a gas conducted from a tank through the needle or probe rapidly expands, causing extreme cold at the closed end of the needle or probe, which in turn, is pressed against the target lesion. In order to attain cryogenic treatment temperatures, these probes and needles use high input pressures up to 100 psi for nitrogen or up to over 1,000 psi for argon, for example. The high pressure may increase throughput compared to low pressure systems, but such high pressures carry inherent dangers and typically require the probe systems to have larger profile needles. Consequently, such probes and needles, which are often delivered to a target lesion through the working channel of an endoscope or bronchoscope or the like, are generally too large in diameter to traverse through airway passages at the distal regions of the lung.

There is, therefore, an existing need addressed by the present disclosure for cryosurgery apparatuses, systems and methods of treatment, that couple precision targeting of tissue or lesions in the distal lung, with the use of a guided catheter or probe that can reach distal lung lesions due to reduced tip profile dimensions, and that delivers a pressurized gas that rapidly expands at the catheter or probe tip, causing extreme cold at the tip which is in contact with the tissue or lesion, resulting in cryoablation in the distal lung tissue or lesions.

SUMMARY

The present disclosure in its various embodiments includes cryogenic delivery to distal lung tissue or lesions. It is a primary object of the present disclosure to provide apparatuses, systems and methods of treatment for ablating target tissue in the distal lung of a patient using navigation or guidance.

In various embodiments of the present disclosure, a system for treating a target tissue or lesion in a distal region of a lung of a patient may include an external imager and display configured to obtain multiple scans of a lung of a patient and generate and display from the multiple scans a computerized three-dimensional model of a network of lumens within the lung including the distal region. A system may include a flexible endoscope insertable through the network of lumens to a position proximate the target tissue. The endoscope may include one or more sensors at a distal end of the endoscope configured to generate an output signal that is detectable by the imager. The output signal may be indicative of a current three-dimensional disposition of the distal end of the endoscope relative to the three-dimensional model of the network of lumens. The disposition of the distal end of the endoscope relative to the model may be viewable on the display. A system may include a catheter having a distal end insertable through the flexible endoscope and may be extendable from the endoscope distal end to the site of the target tissue or lesion. A catheter may include a closed-end tip at the catheter distal end configured for delivery of cryoenergy in direct contact with the target tissue or lesion. A catheter may include a gas intake lumen configured to allow the flow of cryogen therethrough under an initial pressure. A catheter may include a structure at the catheter distal end in fluid communication with the gas intake lumen that creates an area of pressure for the cryogen gas lower than the initial pressure, the cryogen gas expandable in the structure to create an active freeze zone at the distal tip of the catheter.

In various embodiments, a system may include a flexible working channel having a distal end that is extendable from the distal end of the endoscope through the network of lumens to a point between the position proximate the target tissue or lesion and the target tissue or lesion. A flexible working channel may include one or more sensors at the channel distal end configured to generate an output signal that is detectable by the imager, the output signal indicative of a current three-dimensional disposition of the distal end of the channel relative to the three-dimensional model of the network of lumens. The disposition of the distal end of the channel relative to the model may be viewable on the display. The catheter may be slidingly receivable within a lumen of the flexible working channel.

In various embodiments, a system may include a catheter having one or more sensors at the distal end thereof. A catheter may have one or more catheter sensors configured to generate an output signal that is detectable by the imager and indicative of positional coordinates defining a current three-dimensional disposition of the distal end of the catheter relative to the three-dimensional model of the network of lumens. The disposition of the distal end of the catheter relative to the model may be viewable on the display. One or more sensors of the endoscope, channel, or catheter, or some combination thereof, may be electromagnetic sensors and the external imager may detect electromagnetic signals. A catheter may have an outer diameter of less than 2 mm at the closed-end tip thereof.

In various embodiments of the present disclosure, a device for transferring cryoenergy to a target tissue in a distal region of a lung of a patient may include a catheter having a proximal end, a distal end, and a lumen extending therebetween. An inlet path may be within the lumen toward the proximal end that may be configured to allow the flow of a cryogen gas therealong at an initial pressure. An aperture may be within the lumen at a distal end of the inlet path. An area may be within the lumen distal to the aperture that is configured to create a lower pressure of the cryogen gas relative to the initial pressure. The inlet path may have a diameter that is smaller than a diameter of the area. The aperture may have a diameter that is smaller than a diameter of the inlet path and the area. An inner jacket may be about the inlet path, the aperture, and the area. An outer jacket may be about the inner jacket. A channel may be between the inner jacket and the outer jacket. The channel may be in fluid communication with the area. The inner jacket may have an outer diameter at a distal end of the inner jacket that is smaller than an outer diameter at a proximal end of the inner jacket. The outer jacket may have an outer diameter at a distal end of the outer jacket that is smaller than an outer diameter at a proximal end of the outer jacket.

A device may include a diffuser at a proximal end of the channel that is in fluid communication with the channel. A vacuum source may be at a proximal end of the channel that is in fluid communication with the channel. A closed tip may be at the distal end of the catheter that is distal to the area. Insulation may be about at least a portion of the device.

In various embodiments of the present disclosure, a method for treating a target tissue or lesion in a distal region of a lung of a patient may include imaging the patient to obtain multiple scans of a lung of the patient. A method may include generating a computerized three-dimensional model of a network of lumens within the lung from the multiple scans that includes the distal region. A method may include guiding a flexible endoscope through the lumen network. A method may include producing an output signal at a distal end of the endoscope, the output signal indicating positional coordinates that define a current three-dimensional disposition of the distal end of the endoscope relative to the three-dimensional model of the lumen network. A method may include displaying the current disposition of the distal end of the endoscope relative to the three-dimensional model of the lumen network. A method may include advancing a flexible working channel from the distal end of the endoscope through the lumen network along a pathway determined by an output signal produced by the distal end of the working channel to a location within the lumen network proximal to the target tissue or lesion, the output signal indicating positional coordinates that define a current three-dimensional disposition of the distal end of the working channel relative to the three-dimensional model of the lumen network. A method may include advancing a catheter having a closed tip at a distal end of the catheter through the working channel to the site of the target tissue or lesion and positioning the closed tip in contact with the target tissue or lesion, The catheter may include (i) a gas intake lumen configured to allow the flow of a cryogen gas therethrough under an initial pressure and (ii) a structure at the distal end of the catheter that creates an area of lower pressure relative to the initial pressure. A method may include flowing a cryogen gas into the catheter under the initial pressure and through the structure, whereby the lower pressure area causes the cryogen gas to expand and create an active freeze zone at the distal end of the catheter. A method may include transferring cryoenergy from the distal end of the catheter to the target tissue or lesion to freeze at least a portion of the target tissue or lesion.

In various embodiments, a method may include allowing or causing the target tissue or lesion to thaw following freezing, each freeze and thaw step comprising a freeze-thaw cycle. In some embodiments, target tissue or lesion may be subjected to a plurality of freeze—thaw cycles. There may be at least two freeze-thaw cycles. The period of time in which the target tissue or lesion is frozen may range from five to ten minutes or more. A catheter may include an outtake lumen and following freezing, cryogen gas may flow back from the distal end of the catheter through the outtake lumen along a path toward a proximal end of the catheter, exiting the catheter at the proximal end outside of the patient.

A method may include a catheter having an outer diameter of less than 2 mm at the closed tip. A catheter may have one or more sensors at the distal end thereof. One or more sensors may generate an output signal indicating positional coordinates that define a current three-dimensional disposition of the distal end of the catheter relative to the three-dimensional model of the lumen network.

In various method embodiments, a catheter may have a closed end that may have a reduced outer diameter at a distal end that may be less than 2 mm, and have an outer diameter throughout its length sufficiently small to enable it to be advanced far enough into the lung to allow the distal end of the catheter to contact and cryoablate target tissue located in the distal lung. A catheter may be a multi-lumen closed end catheter. A catheter may have one or more sensors located at the distal end thereof. The one or more sensors may generate an output signal indicating positional coordinates that define a current three-dimensional disposition of the distal end of the catheter relative to the three-dimensional model of the network of lumens.

In various embodiments, a method for treating a target tissue or lesion in a distal region of a lung of a patient may include advancing an ablation catheter having a closed tip at a distal end of the catheter through a working channel that extends from a distal end of an endoscope. The endoscope and the working channel may have been previously positioned in the lung. A method may include using electromagnetic bronchoscopy to guide the ablation catheter to the target tissue or lesion and positioning the closed tip in contact with the target tissue or lesion. A catheter may include (i) a gas intake lumen configured to allow the flow of a cryogen gas therethrough under an initial pressure and (ii) a structure at the distal end of the catheter that creates an area of lower pressure relative to the initial pressure. A method may include flowing a cryogen gas into the ablation catheter under the initial pressure and through the structure. The lower pressure may cause the cryogen gas to expand and create an active freeze zone at the distal end of the ablation catheter. A method may include transferring cryoenergy from the distal end of the ablation catheter to the target tissue or lesion to freeze the target tissue or lesion. A method may include forming an ice ball as a marker to assist in identifying at least one ablative margin of the target tissue or lesion. The electromagnetic bronchoscopy may include imaging the patient to obtain multiple scans of the lung and generating a computerized three-dimensional model of the lung from the multiple scans that includes the distal region. Advancing the catheter may further comprise guiding the catheter toward the target tissue or lesion with the aid of the model.

BRIEF DESCRIPTION OF THE DRAWINGS

In the drawings, like reference characters generally refer to the same parts throughout the different views. Also, the drawings are not necessarily to scale, emphasis instead being placed upon illustrating principles of the present disclosure. The present disclosure, and exemplary embodiments according to the disclosure, are more particularly described in the following description, taken in conjunction with and in reference to the following drawings, in which.

DETAILED DESCRIPTION

Figure 1:
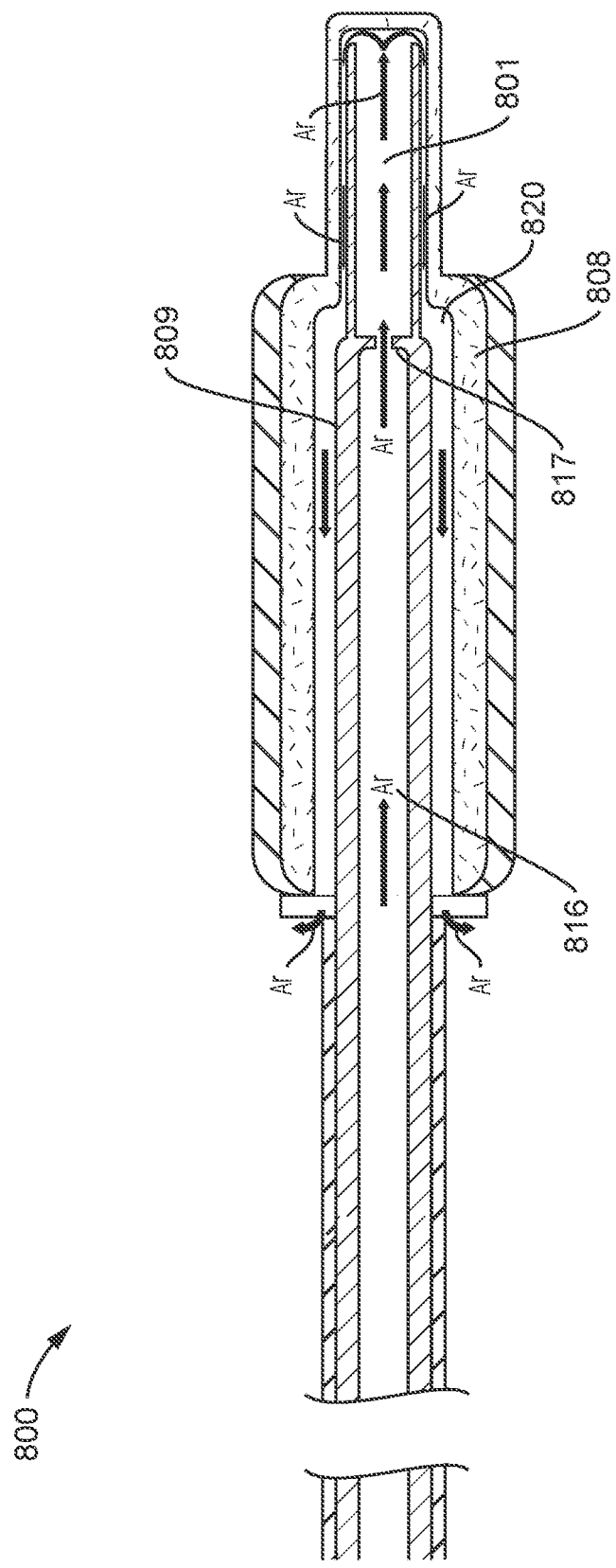
FIG. 1 is a longitudinal cross-section view of a distal construction of a Joule-Thomson cryoprobe according to an embodiment of the present disclosure.

Various embodiments according to the present disclosure are described below with reference to exemplary configurations of systems and devices that may be used in the methods described herein.

In the present systems and methods, cryo ablation is based on the Joule-Thomson effect, in which gas in a region of high pressure travels into an area of lower pressure, thereby allowing the gas to expand and become significantly cooler. Gas, such as argon gas, expands when flowing from an area of high pressure to an area of lower pressure, e.g., flowing through a constricted orifice or aperture (a J-T or Joule-Thomson port) to a wider flow path or simply by flowing under higher pressure from a narrow flow path into a wider flow path. Expansion of the cryogen gas results in ultracold temperatures (approximately −160° C.) at the end of devices. The end of such a device in contact with tissue may be used to transfer cryoenergy to the tissue for ablative purposes, and may be used to form an "ice ball" as a marker to assist in identifying ablative margins of treated tissue.

The present disclosure in its various embodiments is directed to use of navigationally guided cryosurgery systems having cryogen delivery apparatuses, e.g., a catheter, that utilize the Joule-Thomson effect to deliver cryogen gas to a treatment site in the distal lung. The navigationally guided systems may include a flexible endoscope and a flexible working channel for use with the cryogen delivery apparatuses. A cryosurgical system may include a cryogen source configured to provide the cryogen to a cryogen delivery apparatus, a regulation apparatus fluidically coupled to the cryogen source and to the cryogen delivery apparatus, a controller or console with on-board controls communicatively coupled to the regulation apparatus and configured to control the release of cryogen into the cryogen delivery apparatus and a guidance device, system, and/or method that uses one or more imaging devices to acquire images of a patient's lung(s), to provide real-time medical device monitoring, positioning, tracking and/or guidance of the delivery apparatus, alone or in conjunction with a flexible endoscope and/or flexible working channel. The delivery apparatus is a closed-end device, such as a catheter or needle, that may be a multi-lumen device that applies a medical-grade cryogen, such as argon gas or pseudocryogen such as $CO_2$ or nitrous oxide; or other gaseous cryogen, which travels through a lumen from the proximal end of a catheter under high pressure and through a constricted orifice or aperture located at the distal end of the catheter which acts as a throttling device or into an area of lower pressure at the distal end of the catheter, causing the gas to expand at the area of lower pressure (i.e., the Joule-Thomson effect) at a tip of the delivery device, which may be placed in contact with a treatment area.

In the following description, use of the terms catheter, probe, needle or cryogen delivery device alone or together is not to be taken as limiting, but rather is intended to be exemplary in nature. The disclosure in its various embodiments of a delivery apparatus is meant to broadly encompass a delivery apparatus, which may include and take the form of one or more of a catheter, probe, needle or other understood term of art. Also, where used herein, "proximal" refers to the relative position on a device that is closer to the operator during use, while "distal" refers to a relative position on the device that is farther from the operator during use.

As used herein, cryogen refers to any gas that has a sufficiently low boiling point to allow for therapeutically effective cryotherapy and is otherwise suitable for cryogenic surgical procedures. For example, acceptable cryogenic gases may have a boiling point below approximately negative (−) 125° C. The cryogen may be argon or nitrogen, as each is readily available. Other pseudocryogenic gases such as carbon dioxide or nitrous oxide and other gaseous cryogens can also be used.

Alternatively, a mixture of gasses rather than a single gas can be used to enhance the cooling obtained through use of a Joule-Thomson valve. For example, the addition of hydrocarbons to nitrogen can increase the cooling power and temperature drop for a given inlet pressure. Further, it may be possible to reduce the pressure and attain performance comparable to the single gas system at high pressure. Similar to single gas systems, these mixed gas systems have heat exchanger requirements and may be limited in their miniaturization potential by the size of the heat exchanger. The improvement in cooling performance realized by mixed gas systems may be very desirable for medical and other microminiature systems.

Traditional bronchoscopy has helped doctors in the diagnosis of lung cancer and other lung lesions; however, this procedure only allows doctors to reach the central regions of the lung. In the present systems and methods, a navigation system, e.g., utilizing GPS or electromagnetic technology, may be used, which enables access to the outermost areas of the lung while still minimizing invasiveness. Electromagnetic Navigation Bronchoscopy (ENB) procedures are a minimally invasive approach that enable access to difficult-to-reach areas of the lung. In the present systems and methods, ENB may be coupled with the use of a navigation catheter that extends the reach of a bronchoscope. Using a patient's CT lung scan, for example, a navigation system may be used to generate a three-dimensional (3-D or 3D) virtual bronchial tree and allow the physician to map pathways aligned with the patient's anatomy to reach distal pulmonary targets. A virtual roadmap of the patient's lungs and a pathway to a distal nodule or lesion may be created by loading the patient's CT lung scan or other image of the lung onto a computer to be reconstructed into 3D images. This virtual roadmap allows a physician to navigate and guide or steer a cryoablation system including a catheter to the target quickly and accurately. Once the target tissue is reached, the catheter may be extended and the tissue or lesion may be cryoablated.

The catheter guidance devices, systems, and methods may use one or more imaging devices to acquire images, for example, previously acquired ultrasound, CT, MRI, PET and fluoroscopy images, to provide real-time 3D medical device monitoring, positioning, tracking and/or guidance through the lung. Previously acquired images of a patient's lung may also be used in the present methods. For example, acquired images of the patient's lung(s) may be accurately registered to the patient's anatomy in real-time. A guidance device or system, according to systems and method of the present disclosure, such as the Super Dimension™ navigation system, may then show, for example, on a visual monitor or other display system, the locations or positions of sensors located on one or more of an endoscope, extendable working channel, and/or catheter relative to a previously acquired image or images, thereby providing real-time monitoring, positioning, tracking and/or guidance of the endoscope, working channel, and/or catheter relative to an image or images of the patient's lung anatomy.

A guidance device, system, and method that may be used according to one embodiment of the disclosure include the use of a magnetic field. In one embodiment, multiple sensors, e.g., three sensors, are positioned and oriented in different axes of an endoscope, extendable working channel and/or cryoablation catheter, preferably at or near the distal tip thereof catheter, and an external imager or a sensor, e.g., an antenna or antenna pad, is placed in contact with the patient's body, for example, the antenna sensor pad is placed under the prone patient's back. The magnetic field guidance device and method senses or detects the 3-D location of the sensors in the body. The 3-D location of the sensors may then be displayed or represented on a visual monitor or display, for example, as shown on a three-axis coordinate grid. One or more imaging devices may be used to acquire images to provide real-time device monitoring, positioning, tracking and/or guidance. For example, a cryoablation catheter comprising sensor coils may be monitored as the portion of the device comprising the sensor coils is moved through a space, e.g., a distal pulmonary airway, within the patient. The geometry of the space may then be mapped and displayed, for example, on a visual monitor or display, and subsequent or real-time navigation and guidance of devices within the space may then be monitored and displayed relative to the map or model. The terms "sensor" or "sensors" as used throughout the description in reference to being included on a distal end of an endoscope, extendable working channel, or catheter, or some combination thereof, and generating an output signal detectable by an external imager or sensor for the signal, are meant to broadly encompass components such as magnets, coils, antennae, sensors, transmitters, and the like, which are capable of generating a signal, beam or field indicative of positional coordinates of the device to which the sensors are attached.

In a first step of a method in accordance with the present disclosure, an imaging device acquires one or more images, as described herein, of a patient's anatomy of interest, e.g., a lung, and a 3-D bronchial map of the patient's lung is generated therewith. In the event that a lesion in the distal region of the lung is suspected or detected, a bronchoscope is inserted into the airway upstream of the lesion. A flexible working channel (or sheath) containing an electromagnetic guidance device, e.g., sensors attached to the distal surface of the working channel, may then be extended from the distal end of the bronchoscope using electromagnetic guidance correlated with the acquired 3D image of the lung. The working channel becomes a pathway to the target tissue or lesion for subsequent diagnosis and treatment. The bronchoscope, in addition to the flexible working channel (or sheath) may contain an electromagnetic guidance device, e.g., sensors attached to the distal surface of the bronchoscope, for purposes of using electromagnetic guidance correlated with the acquired 3D image of the lung to guide and monitor the position of the bronchoscope. Finally, a closed tip cryoablatio catheter having an appropriate outside diameter (OD), e.g., of less than 2 mm at its distal end, and which may also contain one or more location sensors at or near its distal end, and which may be capable of 360° steering, is inserted through the working channel and guided to and brought into contact with the tissue or lesion.

Once the cryoablationdevice is in place, cryogen delivery may be started and maintained for the duration of the procedure with flow, and optionally suction, being operated via manual or automatic controls, such as, respectively, foot pedals, which may be alone or in conjunction with electronic feedback loop control tied to temperature monitoring. Cryogen gas, e.g., argon or nitrogen, flows at high pressure (e.g., 100 to 1000 psi) through the catheter shaft into a Joule-Thompson valve, which may be a porous plug or other aperture axial with and located within the catheter shaft at a transition point near the tip of the catheter where a diameter of the catheter shaft becomes wider distal to the aperture. As the cryogen passes through the constricted aperture into the wider diameter area of lower pressure, it rapidly expands and cools.

In the embodiment of a catheter according to the present disclosure depicted in FIG. 1, cryogen (in the form of argon gas (Ar)) under higher pressure passes along an inlet path 816 through an aperture 817 in a cryoprobe head 800 at the distal end of the catheter to an area of lower pressure 801. The inlet path 816 allows the flow of a cryogen gas therealong at an initial pressure. The area of lower pressure 801 has a larger diameter than the inlet path 816 resulting in a larger volume distal to the aperture 817 than the smaller volume proximal to the aperture 817. The area of lower pressure 801 allows for a lower pressure of the cryogen gas relative to the initial pressure. Alternatively or additionally, the Joule-Thompson effect may occur from the constricted aperture 817 having a lower volume (and higher pressure) than the area of lower pressure 801. The area of lower pressure 801 having a larger volume allows the cryogen to expand, resulting in a significant temperature drop. A gap between an outer jacket 808 and an inner jacket 809 creates a channel 820 between the jackets and defines an outtake lumen flow path for the cryogen after the area of lower pressure 801. Cryogen flows proximally through the channel 820 toward the proximal end of the catheter. The cryogen exits the catheter at the proximal end or, if an optional vacuum source is used, the cryogen is pulled along an outtake lumen through a pump inlet and exits the pump to vent through a pump outlet. Any cryogen gas that converts to liquid during or after the ablation process is completed flows back through an exit or outer lumen, converts to gas and is exited at the proximal end of the outer lumen.

Each cryoablation treatment of a distal lung tissue or lesion typically includes a freeze, thaw cycle and may include two or more consecutive freeze, thaw cycles. By manipulating the time of each freeze and thaw cycle, the zone of ablation and length of time of the cryogenic procedure can be altered. Because the Joule-Thomson effect results in a very rapid and significant temperature drop, the treatment time can be relatively short. For example, the freeze period of a freeze thaw cycle may range from approximately five to ten minutes. However, the freeze and thaw periods can be adjusted as needed, depending on the type of target tissue, size of the target tissue, and the like. At the end of the procedure, helium gas which warms under the Joule-Thompson effect may be used to warm the catheter and facilitate its removal.

Various embodiments of a catheter for use in accordance with the present disclosure are designed to transport cryogen, such as argon gas, from a console under high pressure to a lumen of the catheter that may include therein an aperture that acts as a throttling mechanism or a structure that causes the cryogen to expand as it traverses the aperture or other structure into the distal end of the catheter and in contact with a closed tip, which may be placed in contact with or proximal to a treatment site in the distal lung. The structure within the catheter that causes the gas to expand may simply be a connector between a narrower shaft and wider shaft at or near the distal tip of the catheter. According to one or more embodiments, a catheter may contain a bayonet and connection housing for attachment to a console at its proximal end, a laser cut hypotube to minimize kinking and breaking, and a polymer layer disposed over the hypotube, thereby sealing the catheter, and an insulation layer to protect the user from cold and prevent unwanted changes in temperature.

The hypotube may be spirally cut, imparting radial flexibility while maintaining some axial stiffness and pushability, and the relative flexibility of the hypotube may be, in some cases, variable along the length of the catheter through the use of a variable-pitch spiral cut. This may be accomplished by varying the separation of the spiral or repeated cut pattern, as well as varying the shape of the pattern itself. For instance, the spiral cut may be characterized by a first, relatively large pitch proximally, and a second, smaller pitch more distally, allowing the distal end, and particularly the tip, to bend about a tighter curve than the more proximal portions of the catheter. The strength and flexibility provided by catheters according to these embodiments may allow a user (e.g., a physician) to retroflex the catheter upwards of 180 degrees on one or more sides of the catheter during a treatment procedure, if needed.

A delivery catheter according to various embodiments may be constructed out of hypotubes of different internal diameters mated to each other to make a proximal shaft and a distal shaft, with the distal shaft having the larger inner diameter (ID). The proximal and distal shafts may be joined at a connector, which functions as a pressure regulator or constricting orifice or aperture, which acts as a throttling device, leading to expansion of the cryogen gas when it reaches the area of lower pressure distal to the connector. The pressure regulator may also be a valve or porous plug or other constricting aperture, which impedes the flow of gas there through and causes the gas flowing through to expand, which causes a decrease in temperature.

The distal shaft of the hypotube(s) may have an OD to be able to fit through a working channel of an endoscope, e.g., bronchoscope, and has an OD which is sufficient to reach and fit through distal lung airways, e.g., 2 mm or less.

The hypotubes may be laminated with a polymeric heat shrink which seals the laser cut pattern from the liquid intended to flow inside the catheter. The polymer layer may be any suitable flexible polymer that is substantially gas impermeable (for example fluorinated ethylene propylene or urethane), and may be disposed over the hypotube in the form of one or more extrusion layers attached by means of heat shrinking, or by means of dip coating, melt coating or spray coating.

The cryogen delivery catheter in other embodiments may be constructed of one or more layers of flexible polyimide, surrounded by a stainless steel braid or coil, which is in turn coated with an outer layer of PEBA, such as Pebax. Extrusion of Pebax over the stainless steel braid or coil may allow the Pebax to wick through the pitch of the steel braid or coil, helping to prevent kinking, breaking, or delamination during retroflex of the catheter. The Pebax may also provide a desirable balance between hardness, which is important for smooth sliding of the catheter and general toughness, and softness, which is important for some degree of tackiness which allows the user to feel the movement of the catheter during insertion. The pitch of the stainless steel braid or coil can be configured to be fine enough to afford the required strength, but still allow the Pebax to wick through.

Figure 2:
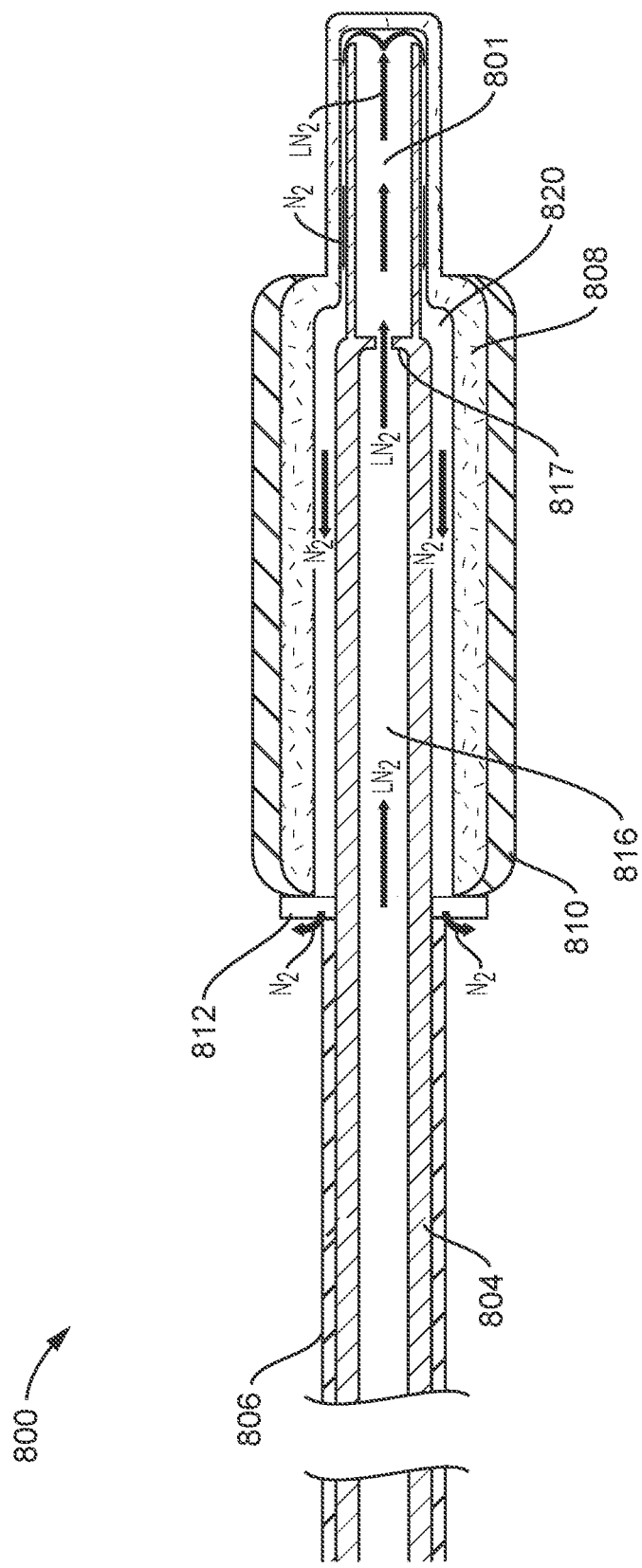
FIG. 2 is a longitudinal cross-section of a distal construction of a Joule-Thomson cryoprobe according to an embodiment of the present disclosure.

FIG. 2 depicts an embodiment of a cryoprobe head 800, in accordance with the present disclosure, at a distal end of a catheter. Liquid cryogen such as liquid nitrogen $LN_2$ flows along inlet path 816, through aperture 817 into an area of lower pressure 801. The inner jacket 804 is surrounded co-axially by an outer jacket 808. The relative inner diameters of the outer jacket and inner jacket are maintained such that a channel 820 forms between the two and defines an outtake lumen flow path. As liquid cryogen exits the area of lower pressure 801 within the inner jacket 804, it travels along the channel 820 to the proximal end of outer jacket 808. A diffuser 812 at the outlet of outer jacket 808 may ensure that any residual liquid nitrogen is converted to gaseous nitrogen $N_2$ before it exits probe head 800. Inner jacket 804 and outer jacket 808 include, respectively, insulation 806, 810 around portions of the exterior of the jackets where an insulating effect is desirable and user and patient exposure to lower temperatures is not desired. Gaseous cryogen exits to the atmosphere directly from diffuser 812, as shown, or may follow a path directed by an optional vacuum source before venting. The diffuser and insulation depicted herein may be used with the embodiment of a catheter depicted in FIG. 1, as well as other embodiments.

The exemplary embodiments described herein, including the dimensions, materials, flow and pressure parameters, are in the context of argon or other cryogen gases as delivered through a delivery catheter, probe or needle that is configured to cause the Joule-Thomson effect as the gas travels therethrough to a treatment site in the distal lung using navigational guidance and visualization. The cryoablation catheter probe may be inserted through a conventional bronchoscope and optionally maneuvered along a guide wire to the target site. Variations on one or more of these parameters, including for example use of a different cryogen source or external navigational and/or visualization device, may be readily determined by one skilled in the art and are within the intended scope of the present disclosure.

Various alternative embodiments of a catheter according to the present disclosure may utilize a vacuum source. Instead of exiting directly to atmosphere at the proximal side of a diffuser, the gaseous cryogen may be continued along an outtake lumen of the outer jacket that is in fluid communication with a pump. A fitting on the extension may transition to a pump inlet leading to the pump. A pump outlet may carry gas from the pump to a vent where the gas may be vented to the atmosphere. Use of a pump or other vacuum source, allows a negative pressure to be applied to the outlet flow path of the gas. A negative pressure (or pressure below atmospheric pressure) may be applied from 0 up to 760 Torr below atmosphere, which is equivalent to 0-14.5 psi of vacuum.

Various shapes, numbers and configurations of closed-tip catheters are contemplated within the scope of the present disclosure. The catheter tip may have blunt contact surface or the tips may be sharp in order that the needle tips may be penetrated into target tissue during cryotherapy.

Exemplary material for the inner and outer jackets include surgical grade stainless steel or nitinol hypotubes that are, for example, laser cut to desired configurations. The closed tip may be surgical grade stainless steel. Exemplary material for insulations include shrink wrap polyimide, FEP, PTFE, and PEBAX, among others. Dimensions and materials for the jackets, insulation and needle tips may be varied in accordance with the present disclosure, and choices for an intended purpose may be readily determined by one skilled in the art in order to optimize a particular configuration or treatment protocol.

Methods according to various embodiments of the present disclosure involve the use of contact cryotherapy, which includes visual guidance of a bronchoscope through the lung. To treat the distal regions of the lung, a physician or other user, in accordance with the various embodiments of the disclosure, attaches the proximal end of a catheter to a source of cryogen, such as by mating a bayonet of the catheter connection housing to a catheter interface, and a gaseous cryogen (e.g., argon) source. In addition to navigational sensors, various other sensor inputs may be attached to the catheter as well, for example a thermocouple. On-board controls may be available for the purpose of, as examples, pre-cooling the catheter, calibrating the system, monitoring pressure in the source tank, monitoring temperature at the catheter distal end and setting the parameters for the cryogen delivery treatment protocol Feedback loop and software controls may be utilized that meter the cryogen delivery based on feedback that is received from the system, for example, dosing parameters calculated based on the maintenance of a certain level of cryogen or cryogen temperatures at the treatment area for predetermined time periods.

Once the proximal end of the delivery apparatus is attached to a cryogen source, and system set-up is complete, the apparatus may be inserted into the body of the patient proximate the treatment site. The catheter may be inserted through the working channel of a bronchoscope. A flexible working channel may be extendable from the bronchoscope and may be integral with or separate from the bronchoscope.

While the examples presented above may be focused on treatment of distal lung tissues, the systems, methods, and principles illustrated thereby, alone or in a system or kit or as part of a method or procedure, including with other accessories, will be understood by those skilled in the art to be applicable to navigationally guided cryotherapy of other systems and conditions within cavities, lumens, tracts, vessels and organs of the body, in which delivery of cryogen to a site, including the esophagus, peritoneal, abdominal, bronchial or thoracic cavities, vasculature, gastrointestinal or urinary tract, uterus, bladder, lung, liver, stomach, duodenum, small intestine, large intestine, rectum, fallopian tube, etc., is desired.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology.

Certain embodiments of the present disclosure have been described above. It is, however, expressly noted that the present disclosure is not limited to those embodiments, but rather the intention is that additions and modifications to what was expressly described herein are also included within the scope of the disclosure. Moreover, it is to be understood that the features of the various embodiments described herein were not mutually exclusive and can exist in various combinations and permutations, even if such combinations or permutations were not made express herein, without departing from the spirit and scope of the disclosure. In fact, variations, modifications, and other implementations of what was described herein will occur to those of ordinary skill in the art without departing from the spirit and the scope of the disclosure. As such, the scope of the present disclosure is not to be limited by the preceding illustrative description, but instead is defined by the following claims.

What is claimed is:

1. A system for treating a target tissue or lesion in a distal region of a lung of a patient comprising:
    an external imager and display configured to obtain multiple scans of a lung of a patient and generate and display from the multiple scans a computerized three-dimensional model of a network of lumens within the lung including the distal region;
    a flexible endoscope insertable through the network of lumens to a position proximate the target tissue, of the endoscope configured to generate a first output signal that is detectable by the imager, the first output signal indicative of a current three-dimensional disposition of the distal end of the endoscope relative to the three-dimensional model of the network of lumens, the disposition of the distal end of the endoscope relative to the three-dimensional model viewable on the display; and
    a catheter having a distal end insertable through the flexible endoscope and extendable from the endoscope distal end to the site of the target tissue or lesion, the catheter comprising:
        a closed-end tip at the catheter distal end configured for delivery of cryoenergy in direct contact with the target tissue or lesion;
        a gas intake lumen configured to allow a flow of cryogen therethrough under an initial pressure; and
        a structure at the catheter distal end in fluid communication with the gas intake lumen that creates an area of pressure for the cryogen gas lower than the initial pressure, the cryogen gas expandable in the structure to create an active freeze zone at the distal tip of the catheter;
        an inner jacket forming comprising the gas intake lumen and the area of pressure;
        an outer jacket about the inner jacket; and
        a channel between the inner jacket and the outer jacket, the channel in fluid communication with the area of pressure.

2. The system of claim 1, further comprising a flexible working channel having a distal end that is extendable from the distal end of the endoscope through the network of lumens to a point between the position proximate the target tissue or lesion and the target tissue or lesion, the catheter configured to generate a second output signal that is detectable by the imager, the second output signal indicative of a current three-dimensional disposition of the distal end of the flexible working channel relative to the three-dimensional model of the network of lumens, the disposition of the distal end of the flexible working channel relative to the model viewable on the display, and the catheter slidingly receivable within a lumen of the flexible working channel.

3. The system of claim 1, wherein the catheter is configured to generate a second output signal that is detectable by the imager and indicative of positional coordinates defining a current three-dimensional disposition of the distal end of the catheter relative to the three-dimensional model of the network of lumens, and the disposition of the distal end of the catheter relative to the model viewable on the display.

4. The system of claim 3, wherein the external imager is configured to detect electromagnetic signals.

5. The system of claim 1, herein the catheter has an outer diameter of less than 2 mm at the closed-end tip thereof.

6. A device for transferring cryoenergy to a target tissue in a distal region of a lung of a patient, comprising:
    a catheter having a proximal end, a distal end, and a lumen extending therebetween;
    an inlet path within the lumen toward the proximal end that is configured to allow a flow of a cryogen gas therealong at an initial pressure;
    an aperture within the lumen at a distal end of the inlet path; and
    an area within the lumen distal to the aperture that is configured to create a lower pressure of the cryogen gas relative to the initial pressure;
    an inner jacket forming the inlet path, the aperture, and the area;
    an outer jacket about the inner jacket; and
    a channel between the inner jacket and the outer jacket, wherein the channel is in fluid communication with the area.

7. The device of claim 6, wherein the inlet path has a diameter that is smaller than a diameter of the area.

8. The device of claim 6, wherein the aperture has a diameter that is smaller than a diameter of the inlet path and the area.

9. The device of claim 6, wherein the inner jacket has an outer diameter at a distal end of the inner jacket that is smaller than an outer diameter at a proximal end of the inner jacket, and wherein the outer jacket has an outer diameter at a distal end of the outer jacket that is smaller than an outer diameter at a proximal end of the outer jacket.

10. The device of claim 6, further comprising a diffuser at a proximal end of the channel that is in fluid communication with the channel.

11. The device of claim 6, further comprising a vacuum source at a proximal end of the channel that is in fluid communication with the channel.

12. The device of claim 6, further comprising a closed tip at the distal end of the catheter that is distal to the area.

13. The device of claim 6, further comprising insulation about at least a portion of the device.

14. A method for treating a target tissue or lesion in a distal region of a lung of a patient, comprising:
    inserting a flexible endoscope into a lung of the patient;
    guiding the flexible endoscope generating a computerized three-dimensional model of a network of lumens within the lung that is generated from multiple scans obtained of the lung that include the distal region;
    producing an output signal at a distal end of the endoscope, the output signal indicating positional coordinates that define a current three-dimensional disposition of the distal end of the endoscope relative to the three-dimensional model of the network of lumens;
    advancing the endoscope through the network of lumens along a pathway determined by the output signal to a location within the network of lumens proximal to the target tissue or lesion;
    advancing a catheter having a closed tip at a distal end of the catheter through the endoscope to the site of the target tissue or lesion and positioning the closed tip in contact with the target tissue or lesion; the catheter comprising (i) a gas intake lumen configured to allow the flow of a cryogen gas therethrough under an initial pressure and (ii) a structure at the distal end of the catheter that creates an area of lower pressure relative to the initial pressure;
    flowing a cryogen gas into the catheter under the initial pressure and through the structure, whereby the lower pressure causes the cryogen gas to expand and create an active freeze zone at the distal end of the catheter; and
    transferring cryoenergy from the distal end of the catheter to the target tissue or lesion to freeze at least a portion of the target tissue or lesion;

wherein structure comprises:
- an inner jacket forming the intake lumen and the area of lower pressure;
- an outer jacket about the inner jacket; and
- a channel between the inner jacket and the outer jacket, the channel in fluid communication with the area of lower pressure.

15. The method of claim 14, further comprising allowing the target tissue or lesion to thaw following freezing, each freeze and thaw step comprising a freeze-thaw cycle.

16. The method of claim 15, wherein each freeze thaw cycle comprises a freeze period of from five to ten minutes.

17. The method of claim 14, wherein the catheter further comprises an outtake lumen and following freezing, cryogen gas flows back from the distal end of the catheter through the outtake lumen along a path toward a proximal end of the catheter, exiting the catheter at the proximal end outside of the patient.

18. The method of claim 14, wherein the catheter is configured to generate an output signal indicating positional coordinates that define a current three-dimensional disposition of the distal end of the catheter relative to the three-dimensional model of the network of lumens.

* * * * *